United States Patent

Kastner et al.

[11] 4,350,636
[45] Sep. 21, 1982

[54] PREPARATION OF PHENYLACETONITRILES CARRYING BASIC SUBSTITUENTS

[75] Inventors: Gerhard Kastner, Ludwigshafen-Maudach; Hardo Siegel, Speyer; Karl-Heinz Geiss, Beindersheim, all of Fed. Rep. of Germany

[73] Assignee: BASF Aktiengesellschaft, Fed. Rep. of Germany

[21] Appl. No.: 296,893

[22] Filed: Aug. 27, 1981

[30] Foreign Application Priority Data

Sep. 11, 1980 [DE] Fed. Rep. of Germany ....... 3034221

[51] Int. Cl.³ .................. C07D 317/60; C07C 121/78
[52] U.S. Cl. .............................. 549/435; 260/465 E; 549/442
[58] Field of Search ...................... 260/340.5 R, 465 E

[56] References Cited

U.S. PATENT DOCUMENTS

| | | | |
|---|---|---|---|
| 3,261,859 | 7/1966 | Dengel | 260/465 E |
| 4,115,432 | 9/1978 | Dengel | 260/465 E |

FOREIGN PATENT DOCUMENTS

| | | |
|---|---|---|
| 986946 | 4/1976 | Canada . |
| 1154810 | 4/1964 | Fed. Rep. of Germany . |
| 1158083 | 6/1964 | Fed. Rep. of Germany . |
| 2059923 | 6/1972 | Fed. Rep. of Germany . |
| 2263527 | 7/1973 | Fed. Rep. of Germany . |
| 2631222 | 1/1978 | Fed. Rep. of Germany . |
| 1367677 | 9/1974 | United Kingdom . |

*Primary Examiner*—Dolph H. Torrence
*Attorney, Agent, or Firm*—Keil & Witherspoon

[57] ABSTRACT

A process for the preparation of phenylacetonitriles, carrying basic substituents, of the formula I

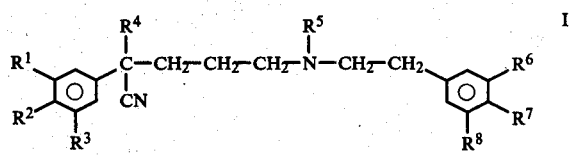

where $R^1$, $R^2$, $R^3$, $R^4$, $R^5$, $R^6$, $R^7$ and $R^8$ have the meanings given in the description, by reacting an aldehyde of the formula II

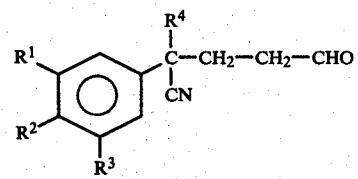

with an amine of the formula III

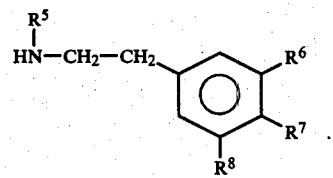

1 Claim, No Drawings

PREPARATION OF PHENYLACETONITRILES CARRYING BASIC SUBSTITUENTS

The present invention relates to a novel process for the preparation of phenylacetonitriles carrying basic substituents.

It is known that phenylacetonitriles carrying basic substituents exhibit coronary-vasodilatory and antiarrhymthmic properties and are therefore valuable drugs for the treatment of various coronary disorders (German Pat. No. 1,154,810, Verapamil).

Various processes are already known for the preparation of phenylacetonitriles carrying basic substituents (German Pat. Nos. 1,154,810 and 1,158,083, German Laid-Open Application DOS 2,059,923, German Published Applications DAS 2,263,527 and DAS 2,631,222 and East German Pat. No. 119,579).

German Published Application DAS 2,631,222 discloses a process for the preparation of phenylacetonitriles carrying basic substituents, which comprises first subjecting an isopropylbenzyl cyanide to condensation with an ω-halo-acetal, then converting the resulting nitrile-aldehyde acetal into the nitrile-aldehyde with aqueous acid and finally subjecting this aldehyde to hydrogenating condensation with an amine.

We have found that the nitrile-aldehyde can also be subjected to condensation with the amine in a Leuckart-Wallach reaction.

The present invention relates to a process for the preparation of phenylacetonitriles, carrying basic substituents, of the formula I

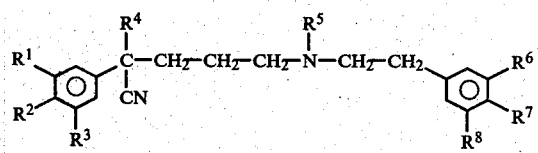

where $R^1$, $R^2$ and $R^3$ are hydrogen, halogen, trifluoromethyl or $C_1$-$C_6$-alkoxy, and $R^1$ and $R^2$ together can also be methylenedioxy, $R^4$ and $R^5$ are $C_1$-$C_6$-alkyl, $R^6$ and $R^7$ are $C_1$-$C_6$-alkoxy or together are methylenedioxy, and $R^8$ is hydrogen or $C_1$-$C_6$-alkoxy, which comprises reacting an aldehyde of the formula II

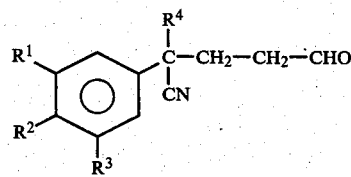

where $R^1$, $R^2$, $R^3$ and $R^4$ have the above meanings, with from 0.8 to 1.5 equivalents of an amine of the formula III

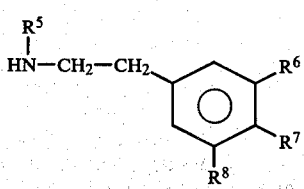

where $R^5$, $R^6$, $R^7$ and $R^8$ have the above meanings, in the presence of from 0.8 to 1.5 equivalents of formic acid at from 20° to 150° C.

The reaction of compounds II and III can be carried out in the presence or absence of an inert solvent. Examples of suitable solvents are water, a lower aliphatic alcohol or diol, e.g. methanol, ethanol, n-propanol, isopropanol, n-butanol, isobutanol, ethylene glycol, 1,2-propylene glycol or 1,3-propylene glycol, a lower saturated dialkyl ether, monoalkyl glycol ether, dialkyl glycol ether or saturated cyclic ether, e.g. diethyl ether, methyl tert.-butyl ether, dipropyl ether, ethylene glycol monomethyl ether, ethylene glycol monoethyl ether, diethylene glycol dimethyl ether, tetrahydrofuran or dioxane, a lower aliphatic ester of a lower aliphatic carboxylic acid, e.g. methyl acetate, ethyl acetate, isobutyl acetate or ethyl propionate, an amide of a lower aliphatic carboxylic acid, e.g. acetamide, N-methylacetamide, N,N-dimethylacetamide or N,N-dimethylformamide, a lactam, e.g. pyrrolidone, N-methylpyrrolidone or caprolactam, a halohydrocarbon, in particular a chlorohydrocarbon, e.g. methylene chloride, chloroform, 1,2-dichloroethane, 1,1,2,2- or 1,1,1,2-tetrachloroethane, 1,1,1-trichloroethane, tetrachloroethylene, propyl chloride, amyl chloride, chlorobenzene, o-, p- or m-dichlorobenzene, o-, m- or p-chlorotoluene or 1,2,4-trichlorobenzene, an aromatic hydrocarbon, e.g. benzene, an alkylated aromatic hydrocarbon, e.g. toluene or xylene, an aliphatic hydrocarbon, e.g. hexane, heptane, octane, dodecane or cyclohexane, or a mixture of the above solvents.

Preferred solvents are water, alcohols of 1 to 6 carbon atoms, e.g. methanol and sec.-butanol, lower saturated dialkyl ethers and cyclic ethers, e.g. diethyl ether, tetrahydrofuran and dioxane, lower aliphatic esters of lower aliphatic carboxylic acids of up to 8 carbon atoms, e.g. ethyl acetate and isobutyl acetate, N,N-dialkylamides of lower aliphatic carboxylic acids, e.g. dimethylformamide and dimethylacetamide, chlorohydrocarbons, e.g. methylene chloride and chloroform, and especially chlorobenzene and o-, m- or p-chlorotoluene, aromatic unsubstituted or alkyl-substituted hydrocarbons, e.g., in particular, benzene, toluene and xylene, and aliphatic hydrocarbons, e.g. hexane, heptane, octane and cyclohexane.

In a preferred embodiment, an aldehyde II is reacted with from 0.9 to 1.3, preferably 1.0 to 1.1, equivalents of an amine III and from 0.9 to 1.3, preferably 1.0 to 1.2, equivalents of formic acid at from 50° to 120° C., preferably at from 50° C. to the reflux temperature of the solvent used.

The reaction mixtures are worked up by one of the conventional methods, such as extraction, crystallization, distillation and/or chromatography.

The process gives high yields and very pure products. Compared with catalytic hydrogenation, the Leuckart-Wallach reaction according to the invention has the advantage that no technically complicated pressure vessels are required and that the reaction procedure is considerably simpler.

It was not to be expected that the Leuckart-Wallach reaction of the aldehydes II would give the products I, since it was known that homoveratrylamine IV and its N-monoalkylated derivatives do not give the desired alkylated amines V but form tetrahydroisoquinolines VI under the conditions of the Leuckart-Wallach reaction:

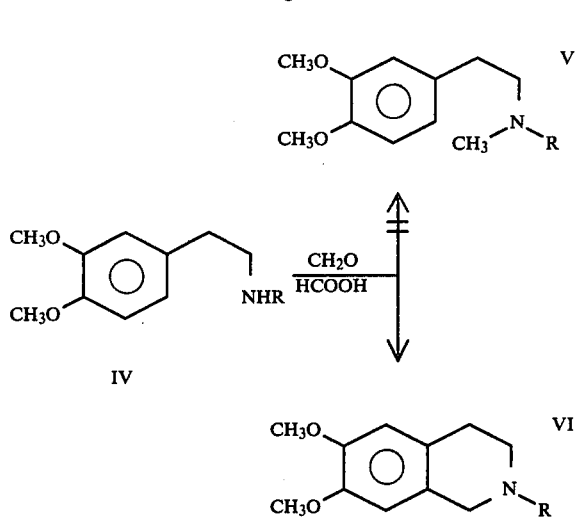

This cyclization reaction is known as the Pictet-Spengler reaction (Org. Reactions 6 (1951), pages 151–190), and proceeds particularly well in the case of electron-rich aromatics.

The different course of reductive alkylation of N-3,4-dimethoxyphenethyl-N-3,4-dimethoxybenzylamine VII under catalysis and under Leuckart-Wallach conditions is demonstrated impressively in Houben-Weyl XI/1, page 644. Whilst the desired methylated amine VIII was formed in the reaction of VII with formaldehyde/Raney Ni/hydrogen, the tetrahydroisoquinoline derivative IX was obtained as the sole product under Leuckart-Wallach conditions:

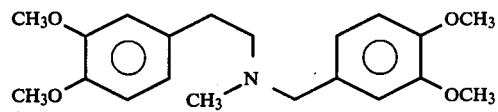

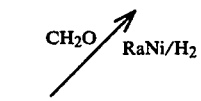

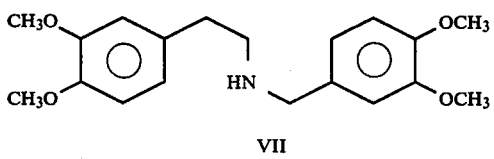

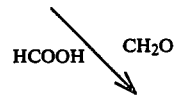

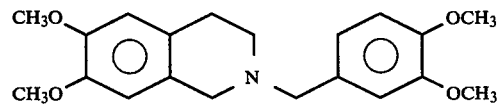

Under Leuckart-Wallach conditions, homoveratrylamine and 3,4,5-trimethoxyphenethylamine behave in a similar manner to VII (Houben-Weyl XI/1, page 652). R. Baltzly, J. Amer. Chem. Soc. 75 (1953), 6038–6039, attempted to carry out the methylation of homoveratrylamine at very low acid concentrations by metering formic acid into a refluxing solution of homoveratrylamine and formaldehyde in a manner such that the pH remained close to 7 and only fell to 5 toward the end of the reaction. In spite of these measures, the yield of N,N-dimethylhomoveratrylamine was only 44%, and 14% of 2-methyl-6,7-dimethoxytetrahydroisoquinoline were also obtained. From his experiments, the author concluded that if the phenethylamine has a structure which favors cyclization, the reaction cannot be steered in such a way that cyclization is completely suppressed.

It is also known that phenethylamines give good to very good yields of correspondingly substituted tetrahydroisoquinolines with electron-rich aromatics (eg. homoveratrylamine) in the presence of acid, not only with formaldehyde but also with aliphatic, aromatic or araliphatic aldehydes (Organic Reactions 6, (1951), 151–190). It was therefore to be expected that, essentially, tetrahydroisoquinolines would be formed in the reaction of aldehydes of the general formula II with amines of the general formula III under Leuckart-Wallach conditions.

EXAMPLE 1

51 g of 90% strength formic acid are added to a solution of 275 g of α-isopropyl-α-(γ-oxopropyl)-veratryl cyanide and 194 g of N-methylhomoveratrylamine (MeHVA) in 1.6 l of toluene and the mixture is refluxed for 1 hour.

When the reaction solution has cooled, the aqueous phase is brought to pH 2–4 with sulfuric acid and extracted with toluene. A second extraction with toluene is carried out after neutralization with NaOH. The toluene phase is washed with water and evaporated in vacuo. The residue is converted into the hydrochloride in isopropanol, and recrystallization from isopropanol gives 395 g (88%) of α-isopropyl-α-[(N-methyl-N- homoveratryl)-γ-aminopropyl]-3,4-dimethoxy-phenylacetonitrile hydrochloride of melting point 141°–143° C.

EXAMPLES 2 TO 12

Examples 2 to 12 in Table 1 were carried out by a method similar to that in Example 1.

TABLE 1

| Example No. | Equivalents of MeHVA | Equivalents of HCOOH |
|---|---|---|
| 2 | 0.9 | 0.9 |
| 3 | 1.0 | 1.0 |
| 4 | 1.0 | 1.1 |
| 5 | 1.0 | 1.2 |
| 6 | 1.0 | 1.3 |
| 7 | 1.0 | 1.5 |
| 8 | 1.05 | 1.05 |
| 9 | 1.1 | 1.1 |
| 10 | 1.1 | 1.3 |
| 11 | 1.5 | 1.0 |
| 12 | 1.5 | 1.5 |

The same product as in Example 1 was obtained in 72 to 86% yield. Example 8 gave the purest product and the best yield. A very pure product was also obtained in Examples 3, 4, 5 and 11.

EXAMPLES 13 TO 17

Examples 13–17 in Table 2 were carried out by a method similar to that in Example 1, at different temperatures.

TABLE 2

| Example No. | Temperature (°C.) | Reaction time |
|---|---|---|
| 13 | 20 | ≧10 hours |
| 14 | 50 | 5 hours |
| 15 | 70 | 2–4 hours |
| 16 | 80 | 1 hour |
| 17 | 100 | 1 hour |

The same product as in Example 1 was obtained in 70 to 86% yield.

EXAMPLES 18 TO 25

Examples 18–25 in Table 3 were carried out by a method similar to that in Example 1, but the toluene was replaced by other solvents.

TABLE 3

| Example No. | Solvent |
|---|---|
| 18 | methanol |
| 19 | sec.-butanol |
| 20 | a 1:4 mixture of sec.-butanol and H$_2$O |
| 21 | tetrahydrofuran |
| 22 | dioxane |
| 23 | ethyl acetate |
| 24 | a 1:4 mixture of dimethylformamide and H$_2$O |
| 25 | chloroform |

Yields of from 70 to 85% were obtained.

EXAMPLE 26

448 g (86%) of α-isopropyl-α-[(N-methyl-N-homoveratryl)-γ-aminopropyl]-3,4,5-trimethoxy-phenylacetonitrile hydrochloride of melting point 145°–147° C. were obtained from 305 g of α-isopropyl-α-(γ-oxopropyl)-3,4,5-trimethoxybenzyl cyanide and 194 g of N-methylhomoveratrylamine in 51 g of 90% strength formic acid by a method similar to that in Example 1.

EXAMPLE 27

470 g (84%) of α-isopropyl-α-[(N-methyl-N-homoveratryl)-γ-aminopropyl]-3-trifluoromethyl-phenylacetonitrile amidosulfonate of melting point 115°–117° C. were obtained from 313 g of α-isopropyl-α-(γ-oxopropyl)-3-trifluoromethylbenzyl nitrile and 194 g of N-methylhomoveratrylamine in 46 g of formic acid by a method similar to that in Example 1.

We claim:

1. A process for the preparation of phenylacetonitriles, carrying basic substituents, of the formula I

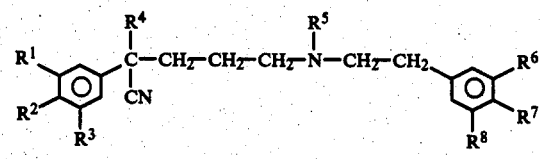

where $R^1$, $R^2$ and $R^3$ are hydrogen, halogen, trifluoromethyl or $C_1$–$C_6$-alkoxy, and $R^1$ and $R^2$ together can also be methylenedioxy, $R^4$ and $R^5$ are $C_1$–$C_6$-alkyl, $R^6$ and $R^7$ are $C_1$–$C_6$-alkoxy or together are methylenedioxy, and $R^8$ is hydrogen or $C_1$–$C_6$-alkoxy, which comprises reacting an aldehyde of the formula II

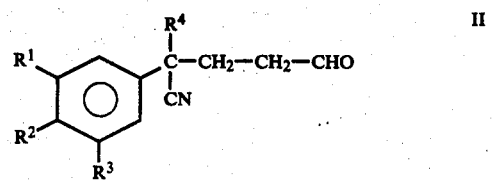

where $R^1$, $R^2$, $R^3$ and $R^4$ have the above meanings, with from 0.8 to 1.5 equivalents of an amine of the formula III

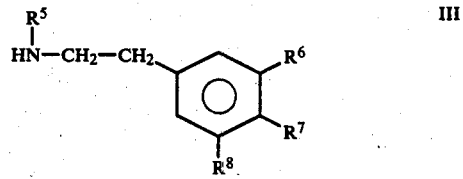

where $R^5$, $R^6$, $R^7$ and $R^8$ have the above meanings, in the presence of from 0.8 to 1.5 equivalents of formic acid at from 20° to 150° C.

* * * * *